US007327306B2

(12) United States Patent
Laroche

(10) Patent No.: US 7,327,306 B2
(45) Date of Patent: Feb. 5, 2008

(54) RF SYSTEM FOR TRACKING OBJECTS

(75) Inventor: Jean-Louis Laroche, Montréal (CA)

(73) Assignee: Orthosoft Inc., Montréal (CA)

(*) Notice: Subject to any disclaimer, the term of this patent is extended or adjusted under 35 U.S.C. 154(b) by 0 days.

(21) Appl. No.: 11/418,114

(22) Filed: May 5, 2006

(65) Prior Publication Data

US 2006/0250300 A1    Nov. 9, 2006

Related U.S. Application Data

(60) Provisional application No. 60/678,190, filed on May 6, 2005.

(51) Int. Cl.
*G01S 13/74* (2006.01)
*G01S 7/40* (2006.01)
*G01S 13/00* (2006.01)
(52) U.S. Cl. .................. 342/126; 342/42; 342/43; 342/118; 342/125; 342/146; 342/147; 342/165; 342/173; 342/175; 342/195; 342/450; 342/451; 600/407; 600/424
(58) Field of Classification Search .......... 342/27–51, 342/175, 195, 450–465, 59, 118, 125, 126, 342/147, 156, 146, 165–174; 606/1, 32–34; 128/897; 600/117, 407, 424, 429
See application file for complete search history.

(56) References Cited

U.S. PATENT DOCUMENTS 2,611,124 A * 9/1952 Hart ............................ 342/33

2,746,034 A * 5/1956 Hasbrook ................... 342/125

(Continued)

FOREIGN PATENT DOCUMENTS

EP    1 034 738    9/2000

(Continued)

OTHER PUBLICATIONS

Tatar, Florin; Molinger, Jeff; Bossche, Andre, *Ultrasound System for Measuring Position and Orientation of Laparoscopic Surgery Tools*, proceedings of IEEE Sensors 2003 (IEEE Cat. No. 03CH37498), IEEE Part vol. 2, 2004, pp. 987-990 vol. 2, Piscataway, NJ, U.S.A.

(Continued)

*Primary Examiner*—Bernarr E. Gregory
(74) *Attorney, Agent, or Firm*—Ogilvy Renault, LLP

(57) ABSTRACT

A system for tracking an object in space for position, comprises a transponder device connectable to the object. The transponder device has one or several transponder aerial(s) and a transponder circuit connected to the transponder aerial for receiving an RF signal through the transponder aerial. The transponder device adds a known delay to the RF signal thereby producing an RF response for transmitting through the transponder aerial. A transmitter is connected to a first aerial for transmitting the RF signal through a first aerial. A receiver is connected to the first, a second and third aerials for receiving the RF response of the transponder device therethrough. A position calculator is associated to the transmitter and the receiver for calculating a position of the object as a function of the known delay and the time period between the emission of the RF signal and the reception of the RF response from the first, second and third aerials. A method is also provided.

15 Claims, 1 Drawing Sheet

U.S. PATENT DOCUMENTS

| | | | | |
|---|---|---|---|---|
| 3,264,644 | A | * | 8/1966 | Jacob .................... 342/125 |
| 3,286,263 | A | * | 11/1966 | Hammack ............... 342/463 |
| 3,308,380 | A | * | 3/1967 | Graves et al. .......... 342/126 |
| 3,339,196 | A | * | 8/1967 | Laurent .................. 342/125 |
| 3,531,801 | A | * | 9/1970 | Huebscher ............. 342/125 |
| 3,953,856 | A | * | 4/1976 | Hammack .............. 342/458 |
| 3,996,590 | A | * | 12/1976 | Hammack .............. 342/465 |
| 4,908,627 | A | | 3/1990 | Santos |
| 5,437,277 | A | | 8/1995 | Dumoulin et al. |
| 5,517,990 | A | * | 5/1996 | Kalfas et al. ........... 600/429 |
| 5,617,857 | A | * | 4/1997 | Chader et al. .......... 600/424 |
| 5,920,261 | A | | 7/1999 | Hughes et al. |
| 6,021,343 | A | * | 2/2000 | Foley et al. ............. 600/429 |
| 6,402,762 | B2 | | 6/2002 | Hunter et al. |
| 6,468,202 | B1 | * | 10/2002 | Irion et al. .............. 600/117 |
| 6,512,478 | B1 | | 1/2003 | Chien |
| 6,618,612 | B1 | | 9/2003 | Acker et al. |
| 6,641,042 | B1 | | 11/2003 | Pierenkemper et al. |
| 6,882,315 | B2 | | 4/2005 | Richley et al. |
| 2003/0018246 | A1 | | 1/2003 | Govari et al. |
| 2003/0132880 | A1 | | 7/2003 | Hintz |
| 2004/0203846 | A1 | | 10/2004 | Caronni et al. |
| 2005/0020279 | A1 | | 1/2005 | Markhovsky et al. |
| 2005/0035897 | A1 | * | 2/2005 | Perl et al. .............. 342/29 |
| 2005/0279368 | A1 | * | 12/2005 | McCombs ............. 128/897 |

FOREIGN PATENT DOCUMENTS

EP    1 329 740    7/2003

OTHER PUBLICATIONS

*MicroBird: Miniaturized Sensor for IntraBody Navigation and Localization*, Ascension Technology Corporation, Burlington, VT, U.S.A., as found on Internet website www.ascension-tech.com.
*LORAN: LOng RAnge Navigation*), as found on Internet website http://www.wordiq.com/definition/LORAN.

* cited by examiner

RF SYSTEM FOR TRACKING OBJECTS

CROSS-REFERENCE TO RELATED APPLICATION

This patent application claims priority on U.S. Provisional Patent Application No. 60/678,190, filed on May 6, 2005, by the present applicant and which is hereby incorporated by reference.

BACKGROUND OF THE INVENTION

1. Field of the Invention

The present invention relates to an RF system for tracking objects in space for position and orientation. The RF tracking system described in this document is used as an example for tracking tools in computer-assisted surgery, but other uses are also contemplated such as mining, storage inventory retrieval, nanorobotics, neurosurgery, cardiology, endodiagnostics, vehicle tracking and any other industrial application.

2. Background Art

It is often required to track objects for position and orientation in space. For instance, in computer-assisted surgery, tools are tracked for position and orientation in order to provide a surgeon with useful data pertaining to relative position between bone elements and surgical tools. For instance, orthopedic surgery involving bone implants benefits from the use of a tracking system that will provide precise information pertaining to alterations to bone elements.

Known tracking systems either offer inadequate precision, or are not completely suited for the types of maneuvers associated with the use of the tracking systems. For instance, in computer-assisted surgery, optical systems are used to track tools. In such systems, a line of sight is required between the tool and movement sensors in order to provide precise position and orientation data. Accordingly, the position of a patient being operated on is influenced by this line of sight that must be kept between the tool and the movement sensors.

Other types of systems, such as magnetic emitters and the like, have been used in computer-assisted surgery. However, such systems typically involve bulky components, or wires that interconnect emitter components. Therefore, considering that the working space in a surgical environment must be sterilized, the use of such systems constitutes a costly solution.

SUMMARY OF INVENTION

It is therefore an aim of the present invention to provide a novel RF system for tracking objects.

It is a further aim of the present invention to address issues of the prior art.

Therefore, in accordance with the present invention, there is provided a system for tracking an object in space for position, comprising: a transponder device connectable to the object, the transponder device having a transponder aerial and a transponder circuit connected to the transponder aerial for receiving an RF signal through the transponder aerial, the transponder device adding a known delay to the RF signal thereby producing an RF response for transmitting through the transponder aerial; first, second and third aerials; a transmitter connected to the first aerial for transmitting the RF signal through the first aerial; a receiver connected to the first, second and third aerials for receiving the RF response of the transponder device therethrough; and a position calculator associated to the transmitter and the receiver for calculating a position of the object as a function of the known delay and the time period between the emission of the RF signal and the reception of the RF response from the first, second and third aerials.

Further in accordance with the present invention, there is provided a method for tracking an object in space for position, comprising the steps of: emitting an RF signal from a fixed position; receiving with a transponder device on the object the RF signal; emitting from the transponder device an RF return signal consisting of the RF signal with a known time delay; receiving the RF signal with at least three aerials associated to the fixed position; and calculating a position of the object from a distance between each of the at least three aerials and the transponder device as a function as a function of the known delay and the time period between the emission of the RF signal and the reception of the RF response from the first, second and third aerials.

BRIEF DESCRIPTION OF THE DRAWINGS

Having thus generally described the nature of the invention, reference will now be made to the accompanying drawings, showing by way of illustration a preferred embodiment thereof and in which.

DESCRIPTION OF THE PREFERRED EMBODIMENTS

Figure 1:
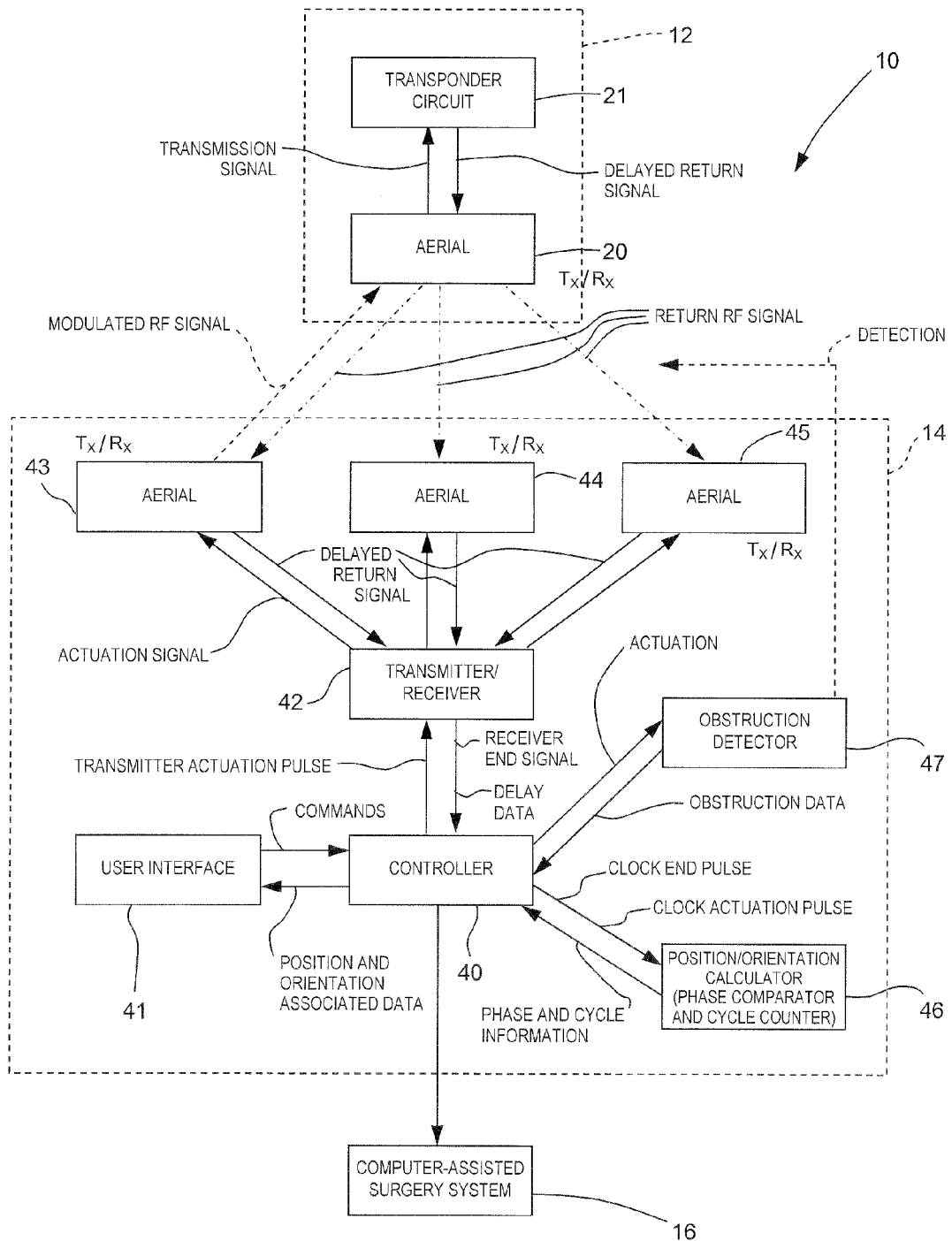
FIG. 1 is a block diagram illustrating a tracking system in accordance with the preferred embodiment of the present invention.

Referring to FIG. 1, a tracking system in accordance with a preferred embodiment of the present invention is generally shown at 10. The tracking system 10 has a transponder device 12 (displaceable, with its independent power source) and a tracking station 14 (fixed). The tracking station 14 is optionally connected to a computer-assisted surgery system 16, or other system requiring position and orientation data that will be produced by the tracking station 14.

The transponder device 12 is connectable to a tool or other object to be tracked in space for position, and orientation if required. The interrelation between the transponder device 12 and the object to be tracked is known (e.g., through calibration) such that a tracking of the transponder device 12 will enable the tracking station 14 to obtain position and orientation information pertaining to the object (e.g., tip of a tool). The transponder device 12 and aerials of the tracking station 14 are typically separated by a distance ranging between 0.5 m to 10.0 m in computer-assisted surgery, but could be more or less depending on the type of application.

The transponder device 12 has an aerial 20 connected to a transponder circuit 21. The aerial 20 is provided to receive incoming RF signals, and to emit response signals as a function of the incoming RF signals, as directed by the transponder circuit 21.

The transponder circuit 21 receives the incoming RF signals and controls the emission of a response through the aerial 20. More specifically, between the receipt of a signal and the transmission of a response signal from the transponder device 12, a delay of time occurs, which delay of time is known. The delay of time is, for instance, caused by one or two SAW filters, a delay line or other delay method on a delay circuit. The transponder circuit 21 may also amplify the incoming RF signal.

The tracking station 14 has a controller 40. The controller 40 is a processing unit (e.g., micro-controller, computer or the like) that controls the operation of the tracking station 14. The controller 40 is connected to a user interface 41, by which an operator may command the tracking system 10. The controller 40 transmits position and orientation associated data to the user interface 41 as output from the tracking system 10.

The controller 40 is also connected to a transmitter/receiver 42. The transmitter/receiver 42 is provided for emitting modulated RF signals through aerials 43, 44 and 45, and for receiving a return RF signal from the transponder device 12 using the aerials 43 to 45.

Accordingly, as shown in FIG. 1, the aerials 43 to 45 are all connected separately to the transmitter/receiver 42. It is preferred to minimize the distance between the transmitter/receiver 42 and the aerials 43 to 45 to minimize any dephasing. However, value tables may be used for the compensation of any delay in transmission due to a non-negligible distance between the transmitter/receiver 42 and the aerials 43 to 45. Operation of the transmitter/receiver 42 is commanded by the controller 40.

A position/orientation calculator 46 is connected to the controller 40. The position/orientation calculator 46 is typically a software or a drive associated with the controller 40, by which position and, if required, orientation pertaining to the transponder device 12 is calculated. Operation of the position/orientation calculator 46 will be described hereinafter.

An obstruction detector 47 is also connected to the controller 40. The controller 40 commands the obstruction detector 47, which will detect any obstruction between the transponder device 12 and the tracking station 14. More specifically, it is possible that obstruction-inducing objects cause interference between the aerials 43 to 45 of the tracking station 14 and the aerial 20 of the transponder device 12. Accordingly, the obstruction detector 47 is provided so as to take into account any obstruction, and any obstruction will be considered in position calculations by compensation software in the position/orientation calculator 46. For instance, noise and the level of the RF signal received by the aerials 43 to 45 is monitored to determine the level of interference, which information is used thereafter by the compensation software. The obstruction detector 47 may signal that a non-negligible level of interference is present (sound signal, visual signal), so as to advise the operator person to remove any interfering object from the field of operation.

The computer-assisted surgery system 16 is optionally connected to the controller 40 (e.g., wireless connection) so as to receive position and orientation data, which will be used by the computer-assisted surgery system 16 in order to provide such information in various forms to the operator of the computer-assisted surgery system 16.

Now that the various components of the tracking system 10 have been described, a general operation of the tracking system 10 follows.

In order to obtain position and, if required, orientation information pertaining to an object, the controller 40 will initiate a transmission to the transponder device 12. The controller 40 will send a signal to the position/orientation calculator 46.

For instance, an actuation pulse is sent to the position/orientation calculator 46. The position/orientation calculator 46 has a cycle counter (i.e., internal clock) and the counter values at the time of transmission (Tx) and at the time of reception (Rx) will be used in the position calculations. Phase measurement is also considered by a phase comparator in the position/orientation calculator 46, as will be described hereinafter.

Simultaneously, a transmitter actuation pulse is sent from the controller 40 to the transmitter/receiver 42. Accordingly, the transmitter/receiver 42 will send an actuation signal to one of the aerials 43 to 45. For instance, the aerial 43 will emit a modulated RF signal (e.g., RF pulse) from this actuation of the controller 40.

The modulated RF pulse from the aerial 43 will be received by the aerial 20 of the transponder device 12. The modulated RF pulse received by the aerial 20 will be forwarded to the transponder circuit 21, which will return the signal in the form of a delayed return pulse emitted by the aerial 20. As mentioned previously, the delay between the receipt of the signal by the aerial 20 and the emission of a return signal by the aerial 20 is known. The modulated RF pulse is a wave train of short length, as a function of the size of the transponder circuit 21.

The modulated RF pulse may be amplified into the delayed return signal. More specifically, in order to reduce the effect of reflections, it is considered to provide gain to the return signal. Any gain at the transponder device 12 is as a function of reception sensitivity of the transmitter/receiver 42. It is also considered to provide a gain as a function of any magnitude loss in the incoming modulated RF pulse.

The emitted return RF signal from the transponder device 12 will be received by all three aerials 43, 44 and 45. Accordingly, by triangulation, the position of the transponder device 12 can be calculated.

Each of the three aerials 43 to 45 will send notification of the delayed return signal to the transmitter/receiver 42, which will forward this receiver end signal to the controller 40.

The controller 40, having received the signal, will actuate the position/orientation calculator 46, by way of an end pulse, so as to obtain a time value for the reception of a signal with cycle counter. The signal will be recognized by the position/orientation calculator 46, whereby the position of the transponder device 12 can be calculated using triangulation with the distance between the aerials 43 to 45 and the transponder device 12. The time delay at the transponder device 12 is taken into account when calculating a distance between the aerials 43 to 45 and the transponder device 12.

It is pointed out that if orientation information is required, the object should be equipped with three of the transponder device 12, in a non-linear arrangement or orthogonal arrangement. Alternatively, a transponder device 12 having three aerials 20 for the transponder circuit 21, via appropriate RF switches can be used. The three transponder aerials would be orthogonally oriented. A single one of the transponder device 12 or the transponder device 12 with a single aerial will provide position information only.

In the event that the position/orientation calculator 46 uses a cycle counter, the amount of time between the emission of the modulated RF pulse and the receipt of the return RF signal by the transmitter/receiver 42 is calculated as a function of the number of cycles measured by the cycle counter. The phase comparator is then used to transform an incomplete remaining cycle into a time value, which will be used to calculate with the number of cycles the total time between emission and reception of a signal by the transmitter/receiver 42.

As mentioned previously, the distance between the aerials and the transponder device 12 is calculated as a function of this time value, and considering the time delay at the transponder device 12 and the speed of light.

Although the tracking station 14 has been described as having three aerials, namely aerials 43 to 45, it is contemplated to provide the transponder device 12 and/or the tracking station 14 with additional aerials to ensure the precision of the position and orientation measurement. Moreover, the type of aerials used can be selected as a function of the level of precision required. In one embodiment, the tracking station 14 typically has a printed circuit board of rectangular shape having aerials at its corners (with circuitry for each aerial), as well as the required circuitry of the transmitted/receiver 42 and other components of the tracking station 14. However, other configurations are contemplated, such as independent printed circuits for each aerial. Any three of the aerials are arranged to form a plane. The signal frequency is typically of 915 MHz. The various actuation signals are of suitable frequency. As an example, it is contemplated to use YAGI aerials for the tracking station 14.

The obstruction detector 47 is connected to the controller 40 so as to feed obstruction data to the controller 40. More specifically, it is contemplated to use a visual sensor (or audio, ultrasound, laser sensors or the like) that will detect the presence of objects between the aerials 43, 44 and/or 45 and the transponder device 12. As a result of any obstruction, the position/orientation calculator 46 will take into account such data in the calculation of the position and orientation of the transponder device 12. If the tracking station 14 is provided with more than three aerials, it is possible to remove signals from one of the aerials in the calculation of the position and orientation by the position/orientation calculator 46, if it is considered that there is obstruction between that given aerial and the transponder device 12. It is contemplated to provide the position/orientation calculator 46 with a database of tabulated information pertaining to the effect of various types of obstruction. This information could be used to correct the position and orientation calculation as a function of the type of obstruction.

The above-described operation of the system involves the emission of a modulated RF pulse by one of the aerials 43 to 45. However, in order to provide constantly updated position and orientation information about the transponder device 12, it is pointed out that the tracking station 14 is constantly cycling modulated RF pulses by sequentially changing the emission from the aerials 43 to 45, or any other suitable sequence.

Other contemplated uses for the tracking system 10 include mining, storage inventory retrieval, nanorobotics, neurosurgery, cardiology, endodiagnostics, vehicle tracking and any other industrial application. It is contemplated to attach the transponder device 12 to a probe. Such a probe could be an injectable probe (e.g., injectable in living beings such as humans and animals).

The invention claimed is:

1. A method for tracking an object in space for position, comprising the steps of:
   emitting an RF signal from a fixed position;
   receiving the RF signal with a transponder device on the object;
   emitting from the transponder device an RF return signal consisting of the received RF signal delayed in time by a known time delay;
   receiving the RF return signal with at least three aerials associated to the fixed position; and
   calculating a position of the object from a distance between each of the at least three aerials and the transponder device as a function of the known delay and the time period between the emission of the RF signal and the reception of the RF return signal from the first, second and third aerials.

2. The method according to claim 1, wherein the step of receiving the RF return signal is performed in three orthogonal axes, such that the step of calculating also involves calculating an orientation of the object.

3. The method according to claim 1, further comprising a step of detecting obstruction before the step of calculating the position of the object, such that position is calculated as a function of the known delay, the time period, and obstruction data.

4. The method according to claim 1, wherein the step of receiving the RF return signal is performed with four aerials, such that the position is calculated as a function of the known delay and the time period between the emission of the RF signal and the reception of the RF return signal from the first, second, third and fourth aerials.

5. The method according to claim 1, wherein the step of calculating the position of the object is performed as a function of a phase difference between the emitted RF signal and the received RF return signal.

6. A system for tracking an object in space for position, comprising:
   a transponder device operatively connected to the object, the transponder device having a transponder aerial and a transponder circuit connected to the transponder aerial for receiving an RF signal through the transponder aerial, the transponder device for adding a known delay to the RF signal for thereby producing an RF response for transmitting through the transponder aerial;
   first, second and third aerials;
   a transmitter connected to the first aerial for transmitting the RF signal through the first aerial;
   a receiver connected to the first, second and third aerials for receiving the RF response of the transponder device therethrough; and
   a position calculator associated to the transmitter and the receiver and having a cycle counter and a phase comparator for calculating a position of the object as a function of the known delay, a number of cycles between the emission of the RF signal and the reception of the RF response from the first, second and third aerials, and as a function of a phase difference between the emitted RF signal and the received RF response.

7. The system according to claim 6, wherein the transponder aerial comprises three orthogonally oriented transponder aerials whereby an orientation of the transponder device is calculated as a function of the RE response of the three transponder aerials.

8. The system according to claim 6, wherein the position calculator has value data associating a distance between at least one of the first, second and third aerial to a time value, whereby the position calculator is for calculating the position as a function of the known delay, the time period and the distance between the at least one of the first, second and third aerial.

9. The system according to claim 6, further comprising a fourth aerial connected to the receiver for receiving the RF response therethrough, with the time period including the reception of the RF response from the fourth aerial.

10. The system according to claim 6, further comprising an obstruction detector associated with the position calculator, the obstruction detector for producing obstruction data, whereby the position calculator is for calculating the position of the object as a function of the known delay, the time period and the obstruction data.

11. The system according to claim 10, wherein the transponder device is for amplifying the RF response, such that the obstruction detector identifies reflective obstructions.

12. The system according to claim 10, further comprising a fourth aerial connected to the receiver for receiving the RF response therethrough, the obstruction detector for considering the RF response received through all of the four aerials to identify obstruction, whereby the obstruction data filters the RF response received through one of the four aerials upon detection of obstruction for said one aerial.

13. The system according to claim 10, wherein the obstruction detector has a sensor device for visually detecting obstructions.

14. The system according to claim 6, wherein the transponder device has a portable power source.

15. The system according to claim 6, wherein said transponder device is switched between three transponder aerials and a transponder circuit is connected to the transponder aerials for receiving RF signals through the transponder aerials, the transponder devices for adding a known delay to the RF signal for thereby producing RE pulses for transmitting through the transponder aerials, further wherein the three transponder aerials are orthogonally oriented.

* * * * *